United States Patent [19]

Castel et al.

[11] 4,016,878
[45] Apr. 12, 1977

[54] HEATER AND HUMIDIFIER FOR BREATHING APPARATUS

[75] Inventors: David Castel, San Diego; Stephen E. Suess, La Jolla, both of Calif.

[73] Assignee: Foundation for Ocean Research, San Diego, Calif.

[22] Filed: June 27, 1975

[21] Appl. No.: 590,820

[52] U.S. Cl. .................. 128/212; 126/204
[51] Int. Cl.² ........................ A61M 16/00
[58] Field of Search ....... 128/212, 186, 192, 142.4, 128/146.3; 126/204; 431/268

[56] References Cited
UNITED STATES PATENTS

| | | | |
|---|---|---|---|
| 2,702,089 | 2/1955 | Engelder | 183/4.8 |
| 2,784,714 | 3/1957 | Pitzipio | 128/146 |
| 2,814,291 | 11/1957 | Holmes | 128/142 |
| 3,045,670 | 7/1962 | Hirtz et al. | 128/192 |
| 3,099,987 | 8/1963 | Bartlett | 128/142 |
| 3,227,208 | 1/1966 | Potter et al. | 165/96 |
| 3,229,681 | 1/1966 | Gluckstein | 128/212 |
| 3,245,459 | 4/1966 | Keith | 431/268 |
| 3,538,908 | 11/1970 | Well et al. | 431/268 |
| 3,820,540 | 6/1974 | Hirtz et al. | 128/212 |

*Primary Examiner*—Robert W. Michell
*Assistant Examiner*—Henry J. Recla
*Attorney, Agent, or Firm*—Brown & Martin

[57] ABSTRACT

A heater and humidifier for use with a breathing mask or other breathing apparatus, to avoid unpleasant and injurious effects of prolonged breathing of cold dry air, or other breathing gas mixture. The action is accomplished by injection and combustion of hydrogen directly in the breathing gas, and is carried out in a safe manner adjacent to or in the breathing mask. In addition to the heating effect, the hydrogen combines with oxygen in the breathing gas to produce moisture. The apparatus is adaptable to use under water, or in the atmosphere at any altitude and can be operated without a special power source.

18 Claims, 5 Drawing Figures

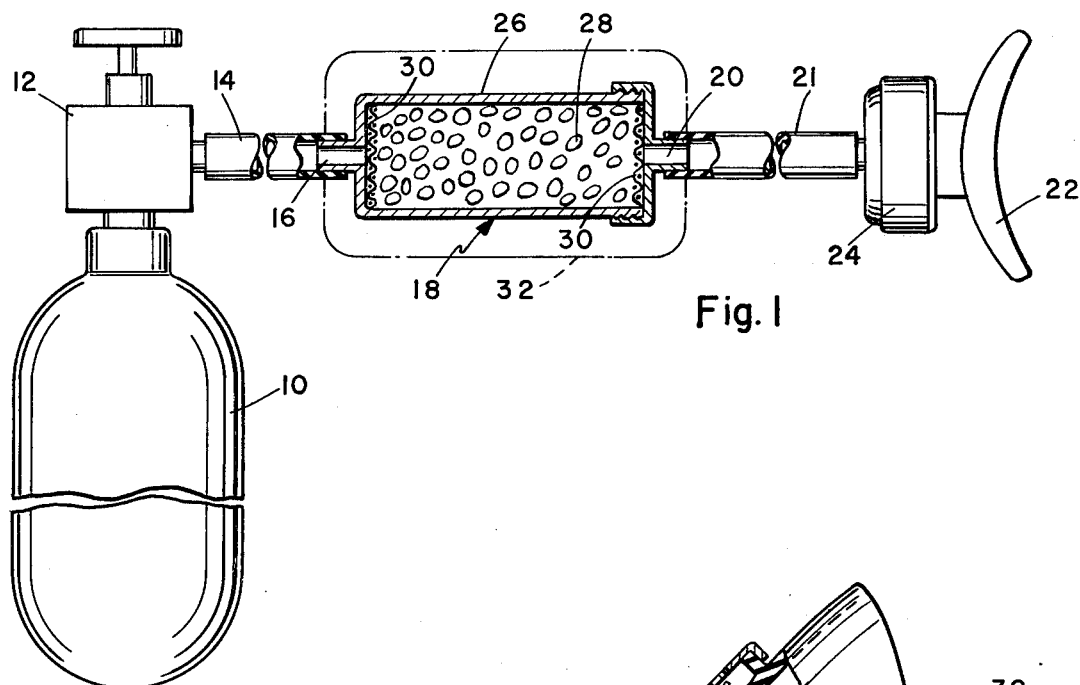
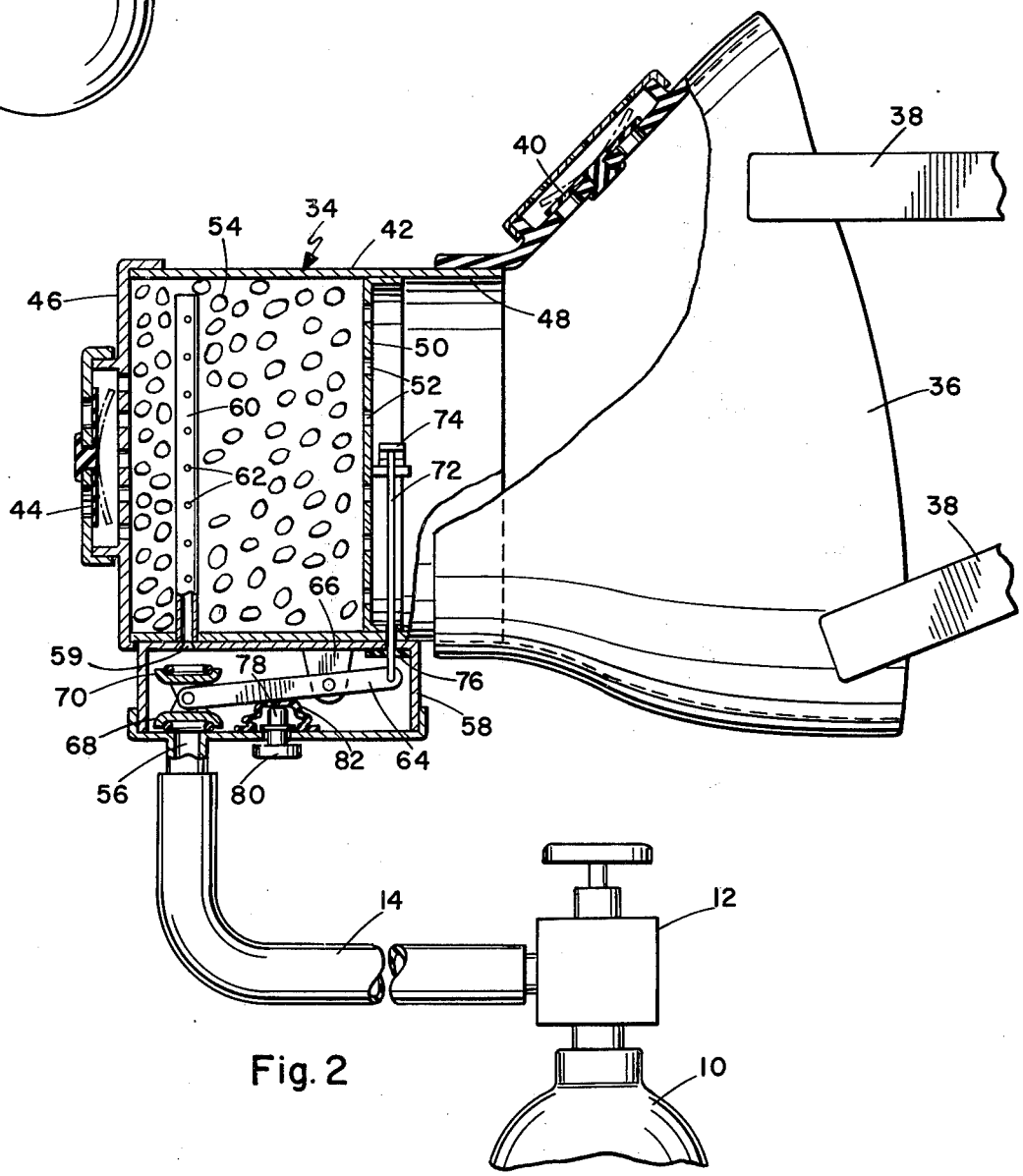

HEATER AND HUMIDIFIER FOR BREATHING APPARATUS

BACKGROUND OF THE INVENTION

In the normal breathing process, inhaled air becomes warmed and humidified as it passes through the nasal, tracheal and bronchial passages. This basic body function protects the delicate membranes in the lungs, but may not be sufficiently effective in heavy or rapid breathing of very cold dry air. During exhalation, some heat and moisture is returned to the walls of the breathing passages, but most of the heat energy and moisture is lost in the exhaled gases.

At rest and at a comfortable room temperature, the energy loss is on the order of 1 Kcal per hour, and is easily compensated by normal body functions. However, as an example, at a temperature of −30° C and at an altitude of 5,500 meters, with a low humidity and at a moderate working rate of 60 breaths a minute, averaging about 2 liters per breath, the loss would be about 230 Kcal and 250 grams of water per hour. This is a significant portion of the body's energy output and the mere use of warm clothing may not be sufficient to retain a desirable amount of the energy. Also, since thirst response is suppressed by extreme cold, dessication could become a problem.

Various techniques have been developed for heating and humidifying breathing gas, but are usually complex and heavy. Thermal heaters require power sources and are not particularly efficient in their use of energy. In a dry atmospheric environment, a humidifier must contain stored water in some form and is thus heavy and bulky. For convenience and reliability, such apparatus should be simple, compact and require a minimum of storable energy producing medium.

SUMMARY OF THE INVENTION

The apparatus described herein is adaptable to breathing masks, mouthpieces and the like used in underwater or atmospheric environments. Typical uses include scuba diving, mountain climbing, operations in arctic or severe winter conditions or cold survival situation, and in aviation and space operations. Generally the uses include any conditions under which air or breathing gas must be used at extremes of cold and low humidity.

The apparatus utilizes a source of hydrogen, preferably in its gaseous form for convenience of storage and utilization. The amount used is very small and a small high pressure cylinder will hold sufficient hydrogen for prolonged use. In the simplest form of the apparatus, the hydrogen is pre-mixed in suitable proportions with the air of breathing gas, in a pressurized container. A heater is installed directly in the line from the supply to the breathing outlet, such as a mouthpiece or mask. The heater is preferably a catalytic type to avoid the need for a power source. Suitable catalysts include metals or metal oxides of platinum, palladium, vanadium, chromium, copper, manganese, cobalt and nickel. These may be coated or supported on carriers such as alumina, magnesia, silica gel, asbestos, diatomaceous earth, or metallic wires such as in screen material.

As the hydrogen containing breathing gas passes over the catalyst, the hydrogen is combusted and heats the gas. In addition, the hydrogen combines with oxygen in the breathing gas and produces water vapor to humidify the gas. As long as the amount of hydrogen is kept below 3% of the total gas content, there is no danger of explosion and the combustion is easily controlled. The amount is more than ample to provide the energy required under all reasonable conditions for which the apparatus is designed.

In other forms, primarily for atmospheric use, the hydrogen is stored in a container and is injected in a controlled amount into the flow of breathing gas. The hydrogen is injected into catalytic material or adjacent to a catalytic or other heating element. For convenience, the structural heating unit may be incorporated in the breathing mask itself. Flow is controlled by a valve which is responsive to the condition of the breathing gas, such as a demand valve operated by the breathing action, or by temperature sensing means which maintains a stable heating condition. While the catalytic type heater is the simplest and most convenient for a portable system, it should be understood that hot wire, flame, or other such ignition means may be used where circumstances permit.

The primary object of this invention, therefore, is to provide a new and improved heater and humidifier for breathing apparatus.

Another object of this invention is to provide a heater and humidifier utilizing the combustion of hydrogen in the breathing gas to generate heat and moisture.

Another object of this invention is to provide a heater and humidifier in which the hydrogen is controlled to maintain the required degree of heating.

A further object of this invention is to provide a heater and humidifier which can be incorporated into a breathing mask.

Another object of this invention is to provide a heater and humidifier utilizing catalytic heating to avoid the need for a power supply.

Other objects and advantages will be apparent in the following detailed description, taken in conjunction with the accompanying drawings, in which:

FIG. 1 illustrates the system in its simple form, with portions of the heating unit cut away.

FIG. 2 is a side elevation view, partially cut away, of a breathing mask incorporating a heating unit with a temperature controlled hydrogen flow control valve.

DESCRIPTION OF THE PREFERRED EMBODIMENTS

Figure 3:
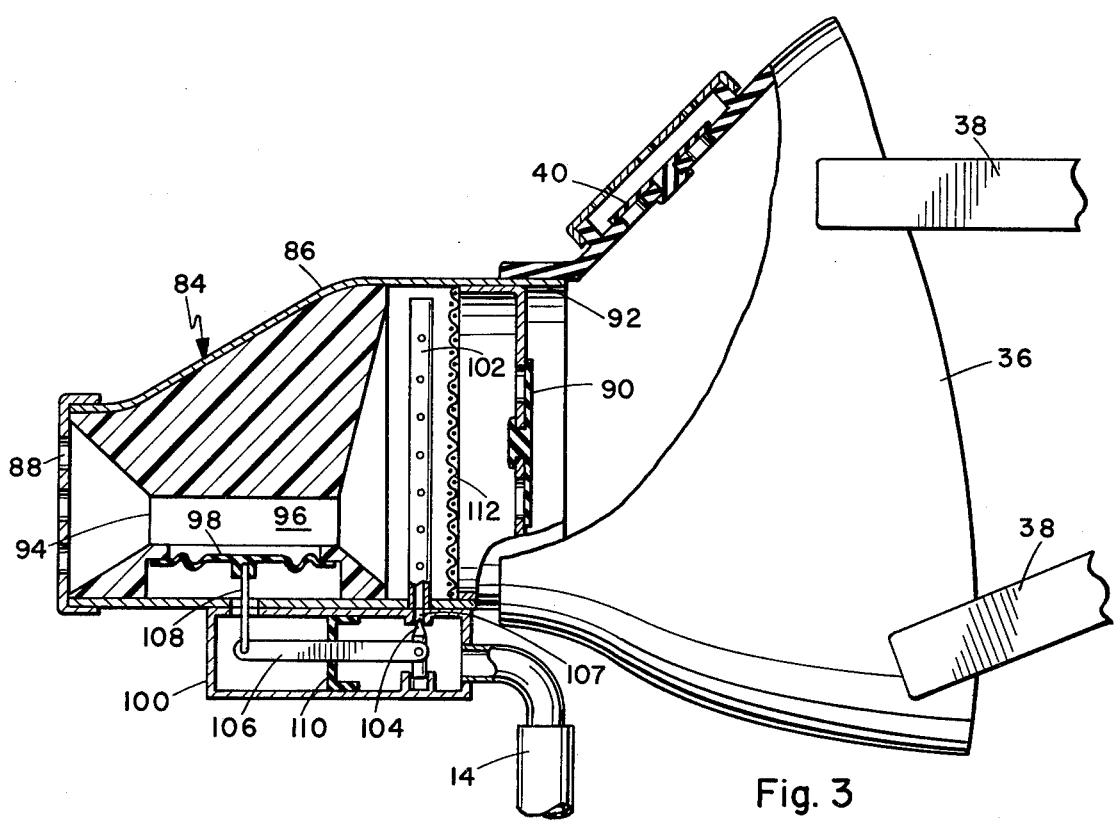
FIG. 3 is a side elevation view of a similar breathing mask, but with a demand type control valve in the heating unit.

In the simple form illustrated in FIG. 1, hydrogen is premixed with breathing gas and stored in a pressurized cylinder or container 10 having a flow control valve or regulator 12. A supply hose 14 leads from valve 12 to the inlet 16 of a heater unit 18. A further hose 21 leads from the outlet 20 of heater unit 18 to a breathing utilization element, illustrated as a mouthpiece 22. The mouthpiece has a demand type valve 24, which passes breathing gas on demand as the user draws a breath. The container 10, regulator 12, mouthpiece 22 and valve 24 are standard items as used in scuba diving equipment.

Heater unit 18 comprises a simple cylindrical canister 26, with tubular inlet and outlet 16 and 20 for attachment of the hoses in any approved manner. The canister 26 contains a catalytic material 28 in granulated or pelletized form which will permit passage of the gas. Screens 30, or similar perforated retainers at opposite ends of the canister prevent the catalytic material 28 from passing through the inlet or outlet. One suitable material for the catalyst is alumina pellets coated with 0.5% platinum, the pellets being about 3 mm in diameter. Other catalytic materials are listed above and various combinations may be used.

In one particular system, about 10–15 grams of platinum coated alumina pellets were used and required about 15–20 minutes to reach a stable operating temperature. Initial warm up can be accelerated by external heating, the amount of heat required being small, such as obtained by holding the canister under the user's arm. With the hydrogen premixed in the breathing gas, the temperature increase obtained is predetermined, but can be controlled to some extent by addition or removal of insulation 32 around canister 26.

Figure 4:
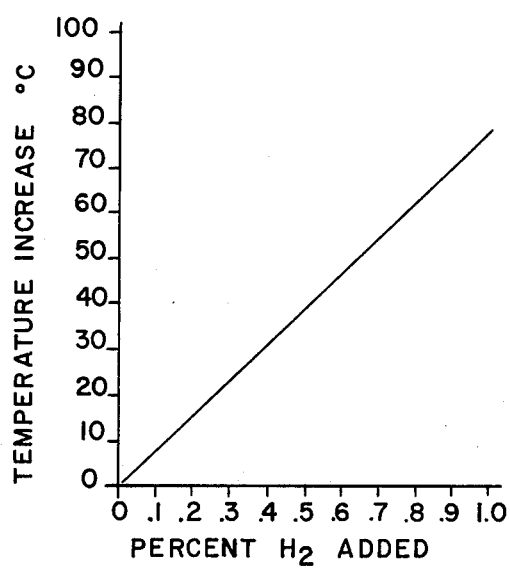
FIG. 4 is a graph showing the relationship of hydrogen input to temperature.
Figure 5:
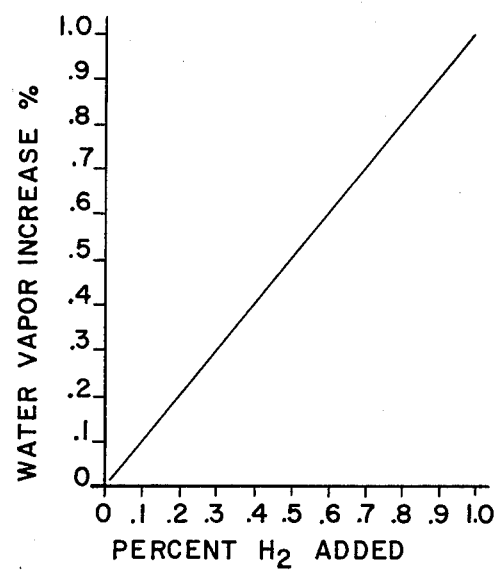
FIG. 5 is a graph showing the relationship of hydrogen input to humidity.

The amount of hydrogen in the breathing gas is small and non-explosive, the maximum desirable amount being about 3%. As illustrated in the graph in FIG. 4, the addition of 0.1% of hydrogen to the basic breathing gas will produce an ideal temperature increase of 7.8° C, or 78° C for a 1% addition of hydrogen. The actual temperature increase will depend on system efficiency and control of heat losses. From the graph of FIG. 5, it can be seen that the addition of 1% of hydrogen causes a nominal introduction of 1% in water vapor.

The temperature change is constant at any ambient pressure and is thus essentially predictable at any altitude on land or any depth in the ocean. However, the humidity change is dependent on temperature and pressure, according to the equation:

$$r = \frac{\%H_2O/100 \times Pa}{Pv} \times 100$$

where
  $r$ is the relative humidity
  $Pa$ is the ambient pressure of the gas being breathed in mm of mercury
  $Pv$ is the vapor pressure of water at the existing gas temperature.

At sea level and room temperature, a 0.1% increase in water vapor is equivalent to approximately 3% increase in relative humidity. From the equation, this becomes about 1.5% at 5,500 meters altitude and about 6% at twice atmospheric pressure, as under water. Using the same hydrogen to breathing gas ratio, a diver would thus breathe air more saturated in moisture than a mountain climber.

In producing the water vapor, the hydrogen consumes half of its amount of oxygen. In air, or in atmospheric pressure ranges with an oxygen content of up to 20% in the breathing gas, this would be inconsequential. For deep sea diving at high pressures, however, the oxygen content of the breathing gas is quite low, on the order of 1%. A diver using 0.5% of hydrogen in the breathing gas would thus have to add 0.25% of oxygen to the basic mixture for combination with the hydrogen.

As an example of the action of the system in air, at a temperature of −30° C and a relative humidity of 10%, with a breathing rate of 60 breaths per minute at an average of 1.5 liters per breath, the loss is about 190 grams of water and 215 Kcal of energy per hour. To raise the temperature of the breathing air by 60° C, or to +30° C, would require the addition of 0.77% hydrogen. This would also add 0.77% water vapor to the breathing air, which results in the addition of 34 grams of water and 105 Kcal of heat energy per hour. About one liter of hydrogen at 2500 psi would supply this energy increase for about 10 hours. It can be seen that a large portion of the energy loss is replaced and the loss can be decreased by adding more hydrogen, up to 3%, to the breathing gas. The limitation is the maximum temperature of gas which can be comfortably breathed. It should be noted that the heater unit could be extended and incorporated into a portion of a wet suit or clothing to obtain the benefit of the heat produced for body heating.

When control of the hydrogen is required, instead of a set pre-mixed amount, the arrangement of FIG. 2 may be used. The apparatus as shown is designed for use in air and includes a container 10 with a regulator 12 and supply hose 14. In this instance the container holds only hydrogen and can be quite small for ease of portability.

The heater unit 34 is attached directly to a breathing outlet, illustrated as a face mask 36 with securing straps 38. The face mask is provided with a diaphragm outlet valve 40 of conventional type to release exhaled air. Other types of outlet valves may be equally suitable, depending on the overall mask design and purpose.

Heater unit 34 comprises a canister 42 having a diaphragm type inlet valve 44, or similar one way valve, in the closed end 46. The other, or outlet end 48 is open and fits into face mask 36. A baffle plate 50 is inset from the open end 48 and has perforations 52 for breathing gas passage. The enclosed chamber between closed end 46 and baffle plate 50 contains the pelletized catalytic material 54. Hose 14 is connected to the hydrogen source inlet 56 of a valve unit 58, attached to or incorporated into the canister 42, and enclosing a hydrogen inlet 59 in the canister, opposite source inlet 56. A manifold tube 60 extends from inlet 59 into the canister and has perforations 62 to distribute hydrogen across the full width of the canister.

In the valve unit 58 is an actuating arm 64 pivotally mounted on a bracket 66. On one end of arm 64 are back to back valve elements 68 and 70, valve element 68 being positioned to close inlet 56 and valve element 70 being positioned to close the opening to manifold tube 60. The other end of arm 64 is connected by a link 72 to a temperature sensing element 74, mounted on baffle plate 50, or on some other suitable support in the canister. The temperature sensing element is preferably a mechanically actuating type, such as a bimetallic strip or coil which will apply a motion to line 72 as the temperature changes the arrangement being well known. The incoming hydrogen flow is small and the pressure, controlled by regulator 12, will normally be quite low, so valve sealing is not a problem. Link 72 passes through a seal 76 to prevent hydrogen leakage directly into the face mask. Temperature sensing element 74 is set to cause valve element 70 to close manifold tube 60 when the breathing gas exceeds a predetermined comfortable temperature. The temperature actuated control thus provides a safety factor in the operation of the apparatus. At a predetermined low temperature, valve 68 closes inlet 56 to shut off hydrogen flow and protect against a malfunction of the catalyst. Since this means that the hydrogen inlet will be closed when the unit is cold, a starting button 78 is provided to open the inlet and initiate hydrogen flow. Button 78 engages arm 64 so that the holding action of temperature sensing element 74 can be overcome to open valve element 68. The head 80 of button 78 acts as a stop against valve unit 58 to limit the movement of arm 64, so that valve element 70 is not inadvertently closed when starting and that both inlets 56 and 59 are simultaneously open. A small boot seal 82 over button 78 prevents hydrogen leakage. The valve configuration and operation as illustrated should be considered as exemplary, and other arrangements may be used to obtain equivalent action.

In operation, each inhaled breath draws air through inlet valve 44 and through canister 42. Hydrogen emitted from manifold tube 60 reacts in the catalytic material 54 and heats the air, while combining with oxygen in the air to provide moisture. The burst of heat occurring with each intake of breath is moderated by the heat sink capacity of the catalytic material and the output is substantially constant. If the temperature becomes too high, the temperature sensing element 74 causes valve 70 to close and shut off the hydrogen input, so that an explosive mixture cannot build up. The heat remaining in the body of catalytic material warms the incoming air until the temperature drops to a safe operating level. It should be noted that, while the apparatus is illustrated for use in air, which is drawn directly through inlet valve 44, any suitable source of breathing gas can be connected to the inlet of the canister if required.

In an alternative arrangement, illustrated in FIG. 3, hydrogen flow is controlled by a demand type device actuated by the breathing action. The face mask 36 is as described above and hydrogen is supplied through a hose 14, as in FIG. 2.

In this configuration the heater unit 84 comprises a canister 86 having an air inlet 88 at the outer end, and an inlet valve 90 in the open end 92 which fits into mask 36. Air from inlet 88 passes through a venturi 94 having a reduced throat portion 96, to produce a pressure drop in the air flow. In the throat portion 96 is a flexible diaphragm 98, which is drawn into the throat by the pressure drop occuring at each intake of breath.

Attached to the canister 86 is a valve unit 100 to which supply hose 14 is connected, a manifold tube 102 extending from the valve unit across the canister. Hydrogen flow into the manifold tube is controlled by a needle valve 104 mounted on one end of an arm 106, and seating in the hydrogen inlet 107. The other end of arm 106 is connected by a link 108 to diaphragm 98. The arm passes through a resilient wall 110, which acts as a seal to prevent hydrogen back pressure behind diaphragm 98. As illustrated, the wall 110 also serves as a pivot for arm 106, but any other suitable pivotal support may be used.

Each intake of breath pulls diaphragm 96 in and causes needle valve 104 to be opened, releasing hydrogen into the manifold tube 102. Adjacent the manifold tube is a catalytic element 112, shown as a wire screen, which would be coated with catalytic material. Other types of catalyst or ignition means may be used to initiate the hydrogen combustion. The hydrogen is thus supplied on demand by the breathing action, and the amount can be controlled by calibration of the needle valve. Since the hydrogen content is precisely controlled in accordance with the breathing action, the temperature can be properly balanced and there is no need for any heat sink effect to smooth out the heating action. It should be understood that temperature controlled safety means, as in FIG. 2, may be used in conjunction with the pressure actuated valve of FIG. 3.

As illustrated, the hydrogen is stored in a cylinder under pressure, but could be obtained from other sources such as metal hydrides, or from various chemical reactions where circumstances permit. In some instances light hydrocarbons could be used. The lightest hydrocarbons, such as methane and ethane give off water and carbon dioxide when burned in air, and produce sufficient heat at low concentrations so that the amount of carbon dioxide added to the breathing air is not harmful at low atmospheric pressures.

It will be evident that the controlled hydrogen combustion means can be incorporated in a variety of breathing apparatus, to obtain any required degree of heating, with the added advantage of moisturizing the breathing mixture. The structure is adaptable to many existing systems and installations and is simple to operate and maintain.

Having described our invention, we now claim:

1. A heater and humidifier for adding heat and moisture in a controlled amount to a breathing gas, such as air, for use in a human breathing apparatus, comprising:

means for providing a supply of hydrogen and oxygen breathing gas with the hydrogen being less than three percent of the combined mixture, a heater unit having inlet means for connection to said gas source means and an outlet for connection to a breathing utilization element, valve means coupled to said heater unit for controlling the flow of hydrogen and breathing gas, and catalyst means in said heater unit for providing combustion of the hydrogen in the breathing gas adding heat and moisture to the gas passing out through the breathing element.

2. The structure of claim 1, wherein said heater unit comprises a canister;

and said catalyst means is a catalytic material capable of inducing hydrogen combustion.

3. The structure of claim 2, wherein said catalytic material is of pelletized form, said canister having perforated retaining means for holding the catalytic material therein.

4. The structure of claim 2, wherein said catalytic material is a perforated screen element.

5. The structure of claim 2, wherein said inlet means includes a hydrogen inlet in said canister, and distributing means extending from the hydrogen inlet across the catalytic material.

6. The structure of claim 5, wherein said valve means is a valve means is a valve mounted at said hydrogen inlet;

and actuating means connected to said valve for opening and closing the hydrogen inlet selectively.

7. The structure of claim 1, wherein said valve means includes a hydrogen flow control valve mounted on the heater unit, and heat sensitive actuating means in the heater unit coupled to said hydrogen flow control valve for shutting off the hydrogen at present extremes of temperature.

8. The structure of claim 1, wherein said valve means includes a hydrogen flow control valve mounted on the heater unit, and pressure sensitive actuating means mounted in the heater unit exposed to the breathing gas flow therein, said actuating means being coupled to the hydrogen flow control valve to provide hydrogen flow at each pressure change caused by breathing action.

9. The structure of claim 1, wherein said heater unit comprises a canister having a closed end with a breathing gas inlet herein, and an open outlet end for attachment to a face mask;

said inlet means including a hydrogen inlet in said canister;

and said valve means comprises a valve unit attached to the canister enclosing said hydrogen inlet, the valve unit having a hydrogen source inlet.

10. The structure of claim 9 and including a hydrogen distributing, perforated manifold tube extending from said hydrogen inlet across the canister.

11. The structure of claim 10 and wherein said catalytic material is in pelletized form surrounding said manifold tube.

12. The structure of claim 10, wherein said catalytic material is a perforated screen extending across the canister between said manifold tube and said open end.

13. The structure of claim 9, wherein said valve means includes a valve element movably mounted in said valve unit for selectively opening and closing said hydrogen inlet;

and actuating means in the canister, responsive to the condition of the breathing gas therein, said actuating means being connected to said valve element.

14. The structure of claim 13, wherein said actuating means comprises temperature sensing means responsive to the temperature of the breathing gas and being mounted between the catalytic material and said open end.

15. The structure of claim 14, and including a further valve element mounted in the valve unit for selectively opening and closing said hydrogen source inlet and being connected to said actuating means.

16. The structure of claim 15, and including manually operable starting means in said valve unit, coupled to said actuating means for holding both of said valve elements simultaneously in the open position.

17. The structure of claim 13, wherein said actuating means comprises pressure sensitive means responsive to the flow of breathing gas through the canister caused by breathing action.

18. The structure of claim 13, and including a venturi having a reduced throat portion adjacent said breathing gas inlet for conducting breathing gas flow therethrough;

said actuating means comprising a flexible diaphragm mounted in said throat portion, and being connected to said valve element to open said hydrogen inlet in response to a pressure drop caused by gas flow through the throat portion.

* * * * *